United States Patent
Della Valle et al.

(10) Patent No.: US 11,819,511 B2
(45) Date of Patent: Nov. 21, 2023

(54) COMPOSITION OF N-PALMITOYL-ETHANOLAMIDE AND RUTIN IN CO-MICRONIZED FORM

(71) Applicant: EPITECH GROUP S.P.A, Milan (IT)

(72) Inventors: Francesco Della Valle, Milan (IT); Maria Federica Della Valle, Milan (IT); Gabriele Marcolongo, Milan (IT); Salvatore Cuzzocrea, Milan (IT); Vito Safina, Milan (IT)

(73) Assignee: EPITECH GROUP S.P.A., Milan (IT)

( * ) Notice: Subject to any disclaimer, the term of this patent is extended or adjusted under 35 U.S.C. 154(b) by 0 days.

(21) Appl. No.: 17/002,073

(22) Filed: Aug. 25, 2020

(65) Prior Publication Data

US 2021/0060047 A1 Mar. 4, 2021

(30) Foreign Application Priority Data

Aug. 26, 2019 (IT) .................. 102019000015018

(51) Int. Cl.
| | |
|---|---|
| A61K 31/7048 | (2006.01) |
| A61P 9/00 | (2006.01) |
| A61K 9/16 | (2006.01) |
| A61K 31/05 | (2006.01) |
| A61K 31/16 | (2006.01) |
| A61K 31/19 | (2006.01) |

(52) U.S. Cl.
CPC ............ *A61K 31/7048* (2013.01); *A61K 9/16* (2013.01); *A61K 31/05* (2013.01); *A61K 31/16* (2013.01); *A61K 31/19* (2013.01); *A61P 9/00* (2018.01)

(58) Field of Classification Search
CPC ........ A61K 31/047; A61K 31/164; A23L 1/30
USPC .................................................. 424/638, 489
See application file for complete search history.

(56) References Cited

U.S. PATENT DOCUMENTS

| | | | |
|---|---|---|---|
| 2015/0265568 A1* | 9/2015 | Della Valle .......... | A61K 31/164 424/489 |
| 2016/0030500 A1* | 2/2016 | Giuliani ................ | A61K 36/63 424/638 |

FOREIGN PATENT DOCUMENTS

EP 2985037 A1 2/2016

OTHER PUBLICATIONS

Britti et al., "A novel composite formulation of palmitoylethanolamide and quercitin decreases inflammation and relieves pain in inflammatory and osteoarthritic pain models." BMC Veterinary Research (2017) 12:229 (Year: 2017).*
Petrosino et al., "The pharmacology of palmitoylethanolamide and first data on the therapeutic efficacy of some of its new formulations." British Journal of Pharmacology (2017) 174 1349-1365. (Year: 2017).*
Eschwege, "The dysmetabolic syndrome, insulin resistance and increased cardiovascular (CV) mobidity and mortality in type 2 diabetes: aetiological factors in the development of CV complications." Diabetes Metab 2003,29,6S19-6S27. (Year: 2003).*
Ganeshpurkar et al., "The Pharmaceuticological Potential of Rutin." Saudi Pharmaceutical Journal (2017) 25, 149-164. (Year: 2017).*
Huang et al., "Rutin alleviates diabetic cardiomyopathy and improves cardiac function in diabetic ApoEknockout mice." European Journal of Pharmacology 814 (2017) 151-160. (Year: 2017).*
Rinne et al., "Palmitoylethnolamide Promotes a Proresolving Macrophage Phenotype and Attenuates Athersclerotic Plaque Formation." Arteriosclerosis, Thrombosis, and Vascular Biology vol. 38, No. 11 published Sep. 27, 2018 (Year: 2018).*
Li et al., "Inhibition of vascular smooth miscle cells premature senescence with rutin attenuates and stabilizes diabetic atherosclerosis." Journal of Nutritional Biochemistry 51 (2018) 91-98. published online Sep. 28, 2017 (Year: 2018).*
Italian Search Report for IT Patent Application No. 201900015018, dated Apr. 1, 2020, 7 pages.
Pillarisetti et al. "Pain and beyond: fatty acid amides and fatty acid amide hydrolase inhibitors in cardiovascular and metabolic diseases" Drug Dicsovery Today, vol. 14, Nos. 23/34, Dec. 2009. pp. 1098-1111.
Wang et al. "How natural dietary antioxidants in fruits, vegetables and legumes promote vascular health" Food Research International, 44(2011) 14-22.

* cited by examiner

*Primary Examiner* — Walter E Webb
(74) *Attorney, Agent, or Firm* — Armstrong Teasdale LLP

(57) ABSTRACT

Described herein is a composition based on N-palmitoyl-ethanolamide and Rutin in co-micronized form. In particular, a composition includes a mixture of palmitoyl-ethanolamide (PEA) and Rutin in co-micronized form in which the PEA/Rutin ratio is between 10:1 and 1:1. Pharmaceutical formulations for the treatment of humans and animals are also described. The composition is useable for the treatment of diseases of arteries and arterioles.

11 Claims, 2 Drawing Sheets

COMPOSITION OF N-PALMITOYL-ETHANOLAMIDE AND RUTIN IN CO-MICRONIZED FORM

CROSS-REFERENCE TO RELATED APPLICATIONS

This application claims the benefit of priority to Italian Patent Application No. 102019000015018, having a filing date of Aug. 26, 2019, which is hereby incorporated by reference in its entirety.

FIELD OF THE ART OF THE INVENTION

The present invention relates to a composition based on N-palmitoyl-ethanolamide and Rutin in co-micronized form.

BACKGROUND ART

Vascular remodeling diseases are responsible for several significant adverse vascular events, such as restenosis, hypertension, arteriosclerosis and atherosclerosis; these consist of the growth and migration of vascular smooth muscle cells (VSMC), the proliferation of endothelial cells and the activation of macrophages, which are quickly attracted to the disturbed flow site [Jongstra-Bilen et al J Exp Med. (2006); 203(9):2073-83].

For these reasons, the medical field currently dedicates growing attention to the problems of the complex Neuro-Immuno-Vascular Peripheral System, especially—even if not exclusively—at the level of arterial vessels. These issues may concern:
  a) primarily neuroimmune alterations at the level of an arterial vessel, with acute or subacute onset, which causes painful sensory and motor deficits and which in turn can induce secondary autonomic peripheral nerve fiber injury. These alterations, most often associated with disorders such as rheumatoid arthritis, viral infections, or type II diabetes, are known as vasculitic neuropathies [Gwathmey K G. et al—The Lancet (2014); 13:67-82];
  b) primarily neuroimmune alterations at the level of the miniaturized endoneural compartment with consequent functional injury on the autonomic fibers directed at the vessel wall, particularly arterial vessels. These are very frequent alterations, generally associated with aging and type II diabetes, classified as slowly progressive axonal polyneuropathies [Hanewinckel—Handb Clin Neurol (2016); 138:263-82].

At the endovasal level and in particular in the outermost layers of the vascular wall—particularly in the tunica adventitia and in the tunica media—a neuroimmune response is activated, excited by functional injuries of the sympathetic, efferent and afferent nerve fibers, which innervate the aforesaid tunicas [Guo-Ping Shi et al—Curr Vasc Pharmacol (2013); 11(3):314-26][Rodella L F. et al—Acta Histochem. (2016); 118(3):256-262]. This acute and chronic neuroimmune response is an important risk factor in vascular remodeling processes. This response is also associated with an intense phenomenon of oxidative stress—located above all in the intima region—which together contributes to representing a key event in the development of neointimal hyperplasia after vascular injury/damage [Donners et al Ann Med (2003)35(7); 523-31].

The above is a paraphysiological or frankly pathological phenomenon which occurs very frequently in situations of aging and in dysmetabolic pathologies such as diabetes [Aldarado-Ibanez A. et al—J Diabetes Res (2019); vol 2019] (Shams A. et al—J Nutr Health Aging (2018); 22(9): 1028-1033).

The same type of vascular damage occurs following the complete experimental ligation of the left carotid artery for two weeks in the experimental animal and this allows to use this model to evaluate products active on complex neuroimmune alterations and on oxidative stress at the vascular localization [Kumar et al Arterioscler thromb Biol. (1997); 17(10):2238-44].

The consequences of these phenomena, only reportedly minor, are several and can progressively evolve into diseases which can also be serious: reference is made in particular to changes in the regulation of vascular tone and therefore in blood pressure, platelet adhesion, proliferation of smooth muscle cells, hemostasis. The permanence of these phenomena within the outermost tunicas also determines, due to the effect of proteolytic enzymes released in situ, the formation of lesion areas of the endothelial surface forming the tunica intima with the consequence of allowing and facilitating lipid deposition in certain areas of the internal vessel wall (fatty streak formation) which can also later evolve into plaque rupture with possible thrombus formation [Kovanen P T. Immunol Rev. 2007; 217:105-122)] [Spinas F. et al_Int Immunopathol Pharmacol (2014); 27 (4):517-21].

At the same time, a phenomenon is established which must be kept under constant medical supervision, particularly in elderly and diabetic patients: it is in particular the progressive decrease in the elastic vessel component due to both the activation of elastases and collagenases [Singh et al 2016; Costa et al 2016], and a marked increase in the existing oxidative stress. This results in endothelial dysfunction and damage to the vascular wall which is likely to evolve into progressive aneurysmal dilatation [Denby K J et al—Hearth 2017; 103(22):1760-1769].

As is known, in the Peripheral Nervous System the autonomic nerve fibers which innervate the vascular tunicas are anatomically allocated in the miniaturized endoneural compartment together with the motor and sensitive fibers; in this compartment, the fundamental role of the neuro-immune component has been clarified for some time, which eventually hinders the indispensable dialogue between the nerve fiber and endoneural microcirculation. This entails an increase in pressure in the miniaturized compartment and consequent anoxic injury of the nerve fibers due to the collapse of endoneural microcirculation [Lundborg G. et al—J. Neurol Neurosur Psychy 1983; 46:1119-1124]. The result is a considerable alteration of the action potential of all the nerve fibers allocated in the miniaturized compartment and therefore functional perturbation of the autonomic fibers as well.

SUMMARY OF THE INVENTION

An object of the present invention is a composition containing a mixture of palmitoyl-ethanolamide and Rutin in co-micronized form.

A further object of the invention is a composition containing a mixture of palmitoyl-ethanolamide and Rutin in co-micronized form, further containing a triterpene molecule endowed with high antioxidant activity.

Still another object of the invention is a composition containing a mixture of palmitoyl-ethanolamide and Rutin in co-micronized form, further containing phytochemical compounds characterized by an ORAC (Oxygen Radical Absorption Capacity) index higher than 35,000-40,000 μmolTE/g.

The mixture of palmitoyl-ethanolamide and Rutin in co-micronized form will be indifferently referred to as "PEA-Rutin micro-compound".

These and further objects, as outlined in the appended claims, will be described in the description which follows. The text of the claims must be considered included in the description for the purpose of assessing the sufficiency of the description.

Further features and advantages of the invention will become apparent from the following description of preferred embodiments, given by way of non-limiting example.

DETAILED DESCRIPTION OF THE INVENTION

Figure 1A:
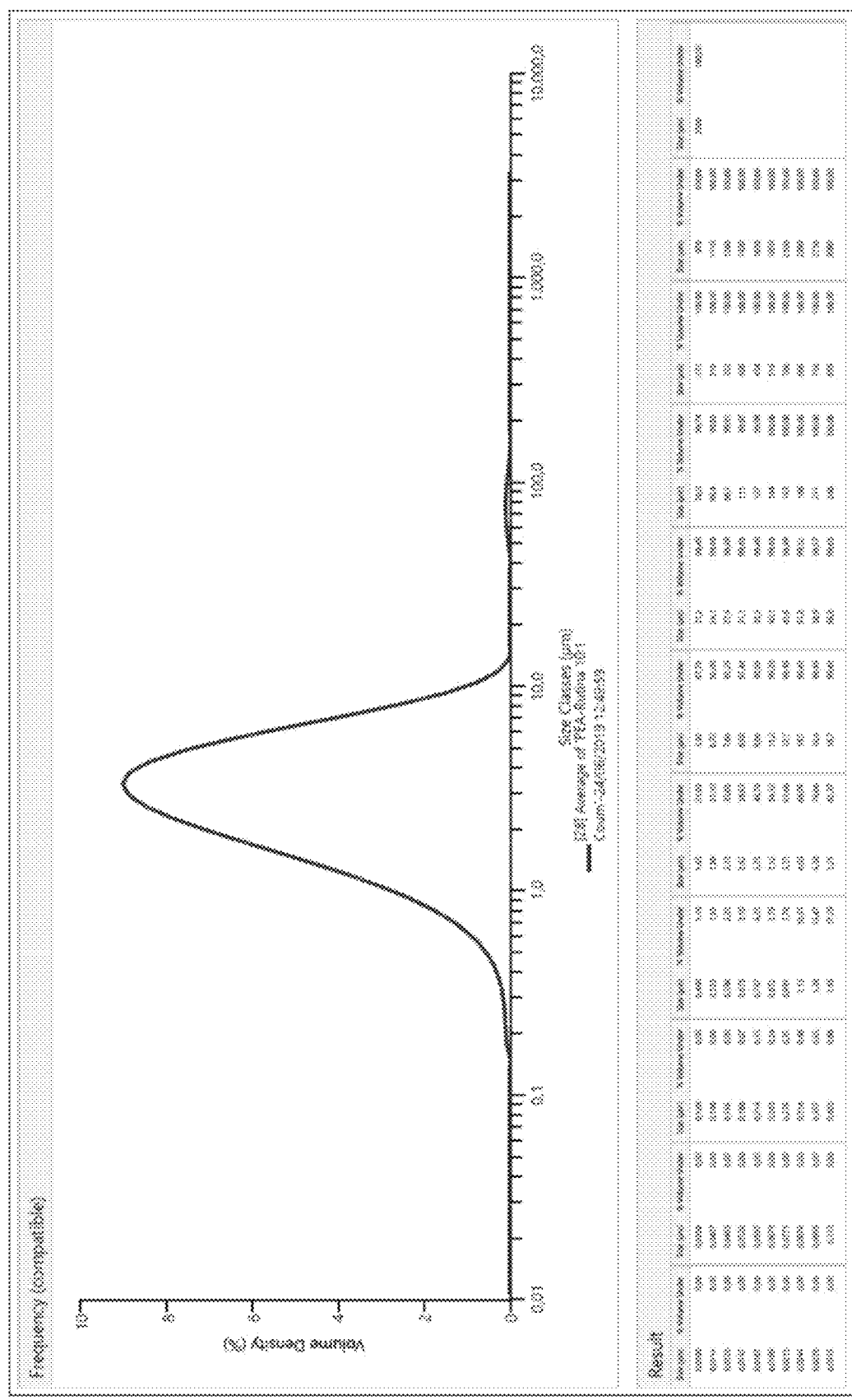
FIG. 1a depicts the graph of particle size distribution of a PEA-Rutin micro-compound in a 10:1 ratio.

The present invention relates in a first aspect to a composition comprising a mixture of palmitoyl-ethanolamide (PEA) and Rutin in co-micronized form.

Rutin, also commonly known as rutoside or oxerutin, is a flavonoic glycoside found in plants such as those of the genus *Citrus*, in buckwheat, in red wine, in peppermint, in eucalyptus, in leaves and petals of the genus *Rheum*, *Sophora* and other plant sources. The glycoside consists of flavonol quercetin (aglycone) bound to disaccharide rutinose and has the following structural formula:

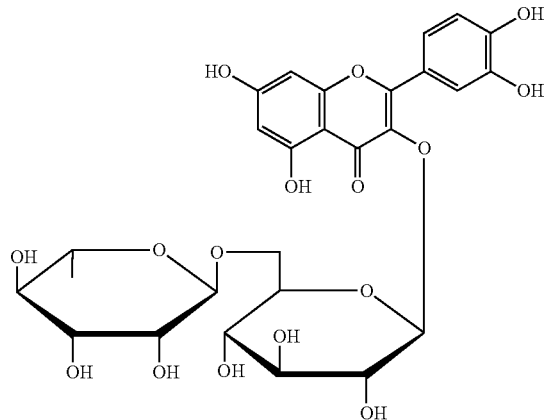

The general term "compounds in co-micronized form" refers to compounds obtained by means of a joint micronization process (i.e., simultaneous micronization of the mixture of said compounds) and having a particle size distribution, defined as a percentage by volume and measured by the laser light scattering method, represented by a distribution curve having the mode below 10 microns but above 0.5 microns.

In one embodiment, the PEA+Rutin mixture in co-micronized form has a particle size distribution as defined above, measured by a Malvern Mastersizer 3000 instrument with Fraunhofer calculation algorithm, where at least 90% by volume of particles has a particle size of less than 10 microns.

In a preferred embodiment, the PEA+Rutin mixture in co-micronized form has a particle size distribution as defined above, measured with a Malvern Mastersizer 3000 instrument with Fraunhofer calculation algorithm, having a mode between 2 and 4 microns and having at least 94% by volume of particles smaller than 10 microns and preferably at least 50% by volume of particles smaller than 4 microns. Two examples of this particle size distribution (PEA-Rutin ratio 10:1 and 1:1 respectively) are reported in FIGS. 1a and 1b.

The micronization can be carried out in a fluid jet system (for example, Jetmill® model system) which operates with spiral technology with a compressed air or nitrogen jet capable of exploiting kinetic energy—instead of mechanical energy—to crush the particles. These apparatuses are conventional and will therefore not be further described.

The mixture of PEA and Rutin in co-micronized form comprises PEA and Rutin in a PEA/Rutin weight ratio between 10:1 and 1:1.

According to a different aspect of the invention, the composition of the invention further comprises a triterpene molecule endowed with high antioxidant activity.

The antioxidant molecule is preferably selected from glycyrrhetinic acid, maslinic acid and ursolic acid.

Glycyrrhetinic acid is an organic pentacyclic triterpene acid, derived from beta-amirins, obtained by hydrolysis of glycyrrhizic acid, which is extracted from licorice and has the following structural formula:

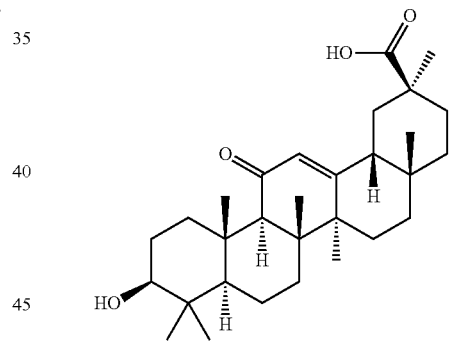

Maslinic acid is a natural antioxidant extracted from the olive tree and has the following structural formula:

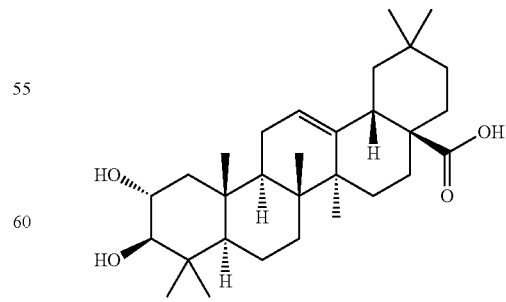

Ursolic acid is a natural antioxidant found in apple peel, blueberries, rosemary, thyme and many other fruits and vegetables and has the following structural formula:

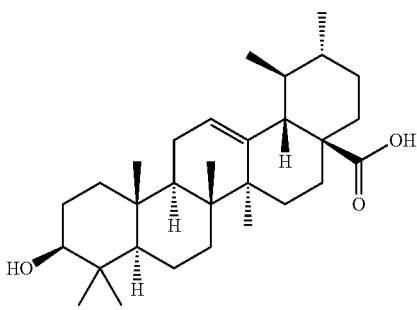

According to another different aspect of the invention, the composition of the invention comprises, in addition to the PEA-Rutin micro-compound, phytochemical compounds characterized by an ORAC (Oxygen Radical Absorption Capacity) index greater than 35,000-40,000 µmolTE/g.

The ORAC assay is based on the measurement of the decrease over time of the fluorescence of a fluorescent target molecule (for example fluorescein) under a constant and controlled flow of radical peroxide, generated by thermal decomposition of an azo-compound. The rate of spontaneous decomposition of fluorescein is slowed down/inhibited by the presence of chain-breaking antioxidants. The reaction is followed for 30 minutes and the quantification of the antioxidant capacity is given by the difference between the area underlying the curve, which represents the oxidation of fluorescein, in the absence and presence of antioxidant (Magalhaes et al., 2008; Lopez-Alarcon & Denicola, 2013) and is generally expressed in Trolox (6-hydroxy-2,5,7,8-tetramethylchromane-2-carboxylic acid) equivalent, i.e., the concentration of a solution of Trolox with an antioxidant capacity equivalent to that found for the tested solution (Magalhaes et al., 2008).

The phytochemical compounds are preferably selected from hydroxytyrosol and the natural oleuropein conjugate thereof.

Hydroxytyrosol (1-(2-hydroxy)ethyl-3,4-dihydroxybenzene) is classified as a phytochemical compound expressing very strong antioxidant properties. The ORAC (Oxygen Radical Absorbance Capacity, i.e., the absorption capacity of the radical oxygen) index for the hydroxytyrosol is equal to 40,000 µmolTE/g, about ten times greater than green tea and at least two times greater than CoQ10 and has the following structural formula:

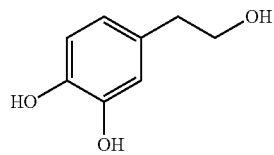

In nature, hydroxytyrosol is found free in high concentrations in the vegetation water of olive trees and in lower concentrations also in the leaves of olive trees or conjugates such as for example in the oleuropein molecule.

Oleuropein is the main polyphenol found in the leaves and fruit of the olive tree; it is found in olive oil both in the form linked to a glucose molecule (glycoside), and in the non-glycated form and has the following structural formula:

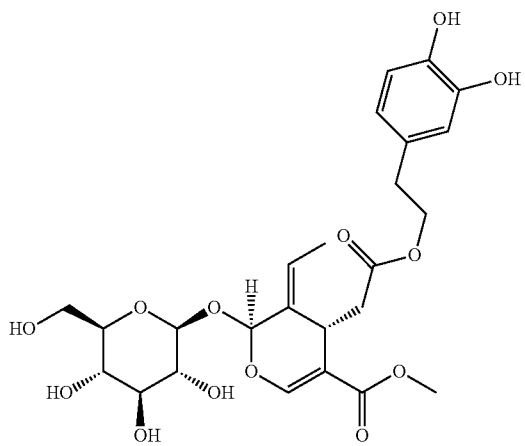 [SMILES: C/C=C1/[C@H](O[C@@H]2O[C@H](CO)[C@@H](O)[C@H](O)[C@H]2O)OC=C(C(=O)OC)[C@H]1CC(=O)OCCc1ccc(O)c(O)c1]

The weight percentage of the aforementioned antioxidant molecules or of the phytochemical compounds as defined above in the composition of the invention is between 1% and 10%.

The composition of the present invention can be used for the treatment of diseases of arteries and arterioles, in particular the diseases generally comprised in codes 170 to 177 of ICD-10 (International Statistical Classification of Diseases of the World Health Organization).

Specifically, the composition of the invention is useable in the treatment of diseases of arteries and arterioles associated with aging and primary dysmetabolic diseases such as Type II diabetes. More particularly, these diseases are preferably selected from:

Atherosclerosis/Arteriosclerosis;
Aortic aneurysms of different localization;
Vasculitic neuropathies;
Slowly progressive axonal polyneuropathies affecting the autonomic nervous system;
Neointimal hyperplasia of different etiology;
Vascular complications associated with the hypokinetic syndrome of the elderly;
Vascular complications associated with the diabetic metabolic syndrome.

A further object of the invention is thus a composition comprising a mixture of PEA and Rutin in co-micronized form, for use in the treatment of diseases of arteries and arterioles as defined above, in humans and animals.

The composition of the invention can be included in pharmaceutical or veterinary formulations and can be formulated in dosage forms for oral, buccal, parenteral, rectal, or transdermal administration.

For oral administration, the pharmaceutical compositions can be found, for example, in the form of tablets or capsules, hard or soft, prepared in the conventional fashion with pharmaceutically acceptable excipients such as binding agents (e.g., pregelatinized cornstarch, polyvinylpyrrolidone or methylcellulose hydroxypropyl); filling agents (e.g., lactose, microcrystalline cellulose or calcium hydrogen phosphate); lubricants (e.g., magnesium stearate, talc or silica); disintegrants (e.g., potato starch or sodium starch glycolate); or inhibiting agents (e.g. sodium lauryl sulfate). The tablets can be coated with the methods well known in the art. The liquid preparations for oral administration can be, for example, in the form of solutions, syrups or suspensions or they can be freeze-dried products to be reconstituted, before use, with water or other suitable vehicles. Such liquid preparations can be prepared through conventional methods with pharmaceutically acceptable additives such as suspending agents (e.g. sorbitol syrup, cellulose derivatives or edible hydrogenated fats); emulsifying agents (e.g. lecithin or acacia); non-aqueous vehicles (e.g. almond oil, oily esters, ethyl alcohol or fractionated vegetable oils); and preservatives (e.g. methyl- or propyl-p-hydroxybenzoates or sorbic acid). The preparation can also conveniently contain flavorings, dyes, and sweetening agents.

The preparations for oral administration can be formulated appropriately to allow the controlled release of the active constituent.

For buccal administration, the compositions can be in the form of tablets or pills formulated in the conventional fashion, adapted to an absorption at the level of the buccal mucosa. Typical buccal formulations are tablets for sublingual administration.

The composition of the invention can be formulated for parenteral administration by injection. The injection formulations can be presented as a single dose, for example in vials, with an added preservative. The compositions can appear in this form as suspensions, solutions, or emulsions in oily or aqueous vehicles and can contain agents of the formulation such as suspension, stabilizing and/or dispersing agents. Alternatively, the active constituent can be found in the form of a powder to be reconstituted, before use, with a suitable vehicle, for example with sterile water.

The composition of the invention can also be formulated according to rectal formulations such as suppositories or retention enemas, for example containing the basic components of the common suppositories such as cocoa butter or other glycerides.

In addition to the compositions described above, the composition of the invention can also be formulated as a deposit preparation. Such long-acting formulations can be administered by implantation (e.g. subcutaneously, transcutaneously or intramuscularly) or by intramuscular injection. Thus, for example, the composition can be formulated with appropriate polymeric or hydrophobic materials (for example in the form of an emulsion in a suitable oil) or ion exchange resins or as minimally soluble derivatives.

According to the present invention, the dose of PEA-Rutin micro-compound proposed for administration to a human (with a body weight of about 70 Kg) ranges from 10 mg to 1000 mg or from 100 mg to 700 mg of the PEA-Rutin micro-compound per dose unit. The dose unit can be administered, for example, 1 to 4 times a day. The dose will depend on the route chosen for administration. It should be considered that it may be necessary to continuously vary the dosage depending on the age and weight of the patient and also on the severity of the clinical condition to be treated. The exact dose and route of administration will ultimately be at the discretion of the attending physician or veterinarian.

A further object of the invention is also dietary compositions, food supplements and foods for special medical purposes (FSMP) comprising the PEA-Rutin micro-compound according to the invention, possibly in the form of the composition with antioxidants and/or phytochemical molecules as previously described.

The term "foods for special medical purposes" refers to products authorized according to the European Commission Directive to Member States no. 1999/21/EC and following. This term refers to a product "intended to meet particular nutritional needs of people affected by a specific disease, disorder or medical condition" in order to cure or help cure the specific medical condition, thereby assimilating this FSMP product to a drug.

The formulations according to the invention can be prepared according to conventional methods, such as those described in Remington's Pharmaceutical Sciences Handbook, Mack Pub. Co., N.Y., USA, 17th edition, 1985.

EXPERIMENTAL PART

Micronization Procedure

The PEA-Rutin mixture was co-micronized as described above.

The micronization and co-micronization were carried out in all cases in a fluid jet system (in particular, the Jetmill® model system) which operates with spiral technology; with compressed air jet technology.

Optimal Micronization Conditions:
internal diameter of the micronization chamber 300 mm;
fluid jet pressure 8 bar;
product supply 20-25 kg/h.

Determination of the Particle Size Distribution

The determination of the particle size distribution was carried out on a wet sample, after 1-minute sonication.

A Malvern Mastersizer 3000 instrument operating with the LALLS (Low Angle Laser Light Scattering) technique and a Fraunhofer calculation algorithm was used.

Figure 1B:
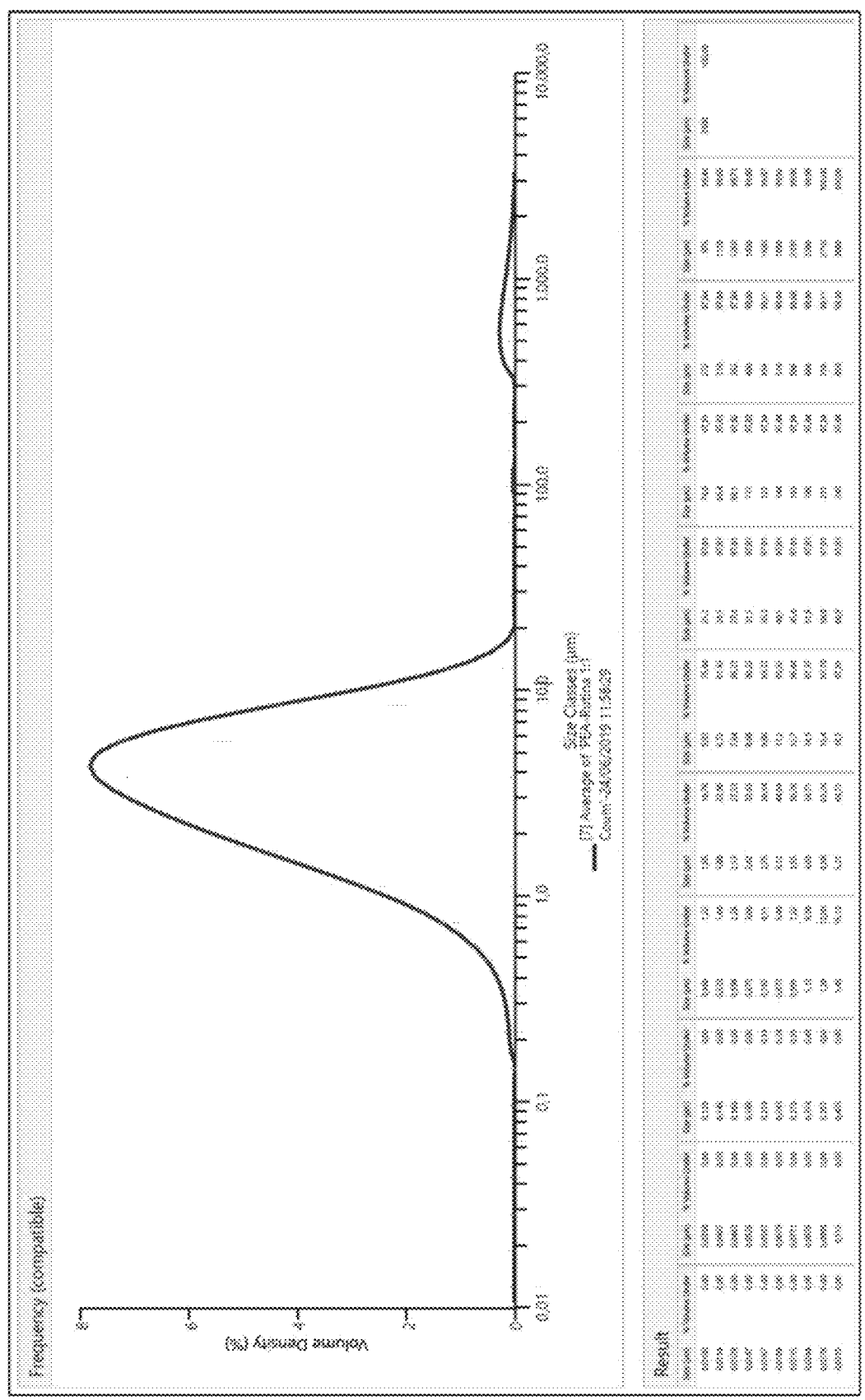
FIG. 1b depicts the graph of particle size distribution of a PEA-Rutin micro-compound in a 1:1 ratio.

The particle size distribution graphs relating to the PEA-Rutin 10:1 and 1:1 ratios, respectively, are shown in FIGS. 1a and 1b.

Biological Experimentation

In order to evaluate the biological effects of the PEA-Rutin micro-compound object of the invention—formed by co-micronization between palmitoyl-ethanolamide and Rutin—on the arterial vessel and the synergy between the two components compared to when administered alone or in a "non-co-micronized" combination, the animal model of complete ligation of the left carotid artery was used for 14 days in adult C57Bl/6 strain mice weighing 25-30 g. (as described by Q.Xu "*Mouse models of arteriosclerosis: from arterial injuries to vascular grafts*" Am J Pathol. (2014); 165(1):1-10).

In particular, vascular reactivity parameters were measured ex vivo on 3-4 mm high thoracic aorta rings exposed to peroxynitrite solution (as described by S. Cuzzocrea et al "*Superoxide: a key player in hypertension*" FASEB J. (2004); 18(1):94-101), collected on day 14 from animals subjected, as mentioned above, to the complete ligation of the left carotid artery, in the various groups of animals treated with the different compounds one hour after ligation and once a day for 14 days.

In particular, the ex vivo measurement of vascular reactivity is carried out with the following procedures:

Adult mice of the C57Bl/6 strain weighing 25-30 g are used (Envigo-Italy). The groups of animals on which the evaluations were carried out (10 animals per group) were the following:

Group 1—Animals treated per os with 10 mg/kg of co-micronized palmitoyl-ethanolamide: Rutin microcompound in a 1:1 ratio, suspended in 1% carboxymethylcellulose solution;

Group 2—Animals treated per os with only 5 mg/kg of micronized palmitoyl-ethanolamide, suspended in 1% carboxymethylcellulose solution;

Group 3—Animals treated per os with only 5 mg/kg of micronized Rutin, suspended in 1% carboxymethylcellulose solution;

Group 4—Animals treated per os with 5 mg/kg of micronized palmitoyl-ethanolamide and, separately, with 5 mg/kg of micronized Rutin, mixed in powder at the moment of use and suspended in 1% carboxymethylcellulose solution;

Group 5—Animals treated per os with only 1% carboxymethylcellulose solution;

Group 6—Animals treated per os with 10 mg/kg of co-micronized palmitoyl-ethanolamide micro-compound: Rutin in a 1:1 ratio, suspended in 1% carboxymethylcellulose solution and with the addition of 0.5 mg/kg of pure hydroxytyrosol in the final solution.

At the end of the treatments, the thoracic aortas of the animals are taken and adequately cleaned of the adherent peri-adventitious fat and 3-4 mm rings are cut out. The rings are placed in Krebs solution at pH 7.4 (Krebs solution composition: NaCl 118 mM; KCl 4.7 mM; $KH_2PO_4$ 1.2 mM; $CaCl_2$ 2.5 mM; $MgSO_4$ 1.2 mM; $NaHCO_3$ 25 mM; glucose 11.7 mM). The isometric force is measured with an isometric transducer (Kent Scientific Corp. USA) digitized using a Maclab A/D converter (AD Instruments USA) and then stored and displayed on a computer. A voltage of 1 g is applied, and the Krebs solution is exchanged every 15 minutes. The aorta rings are exposed to a concentration of peroxynitrile 1 mM. The contraction of the rings themselves is then measured as a response to different concentrations of norepinephrine (100 nM; 1000 nM; 10,000 nM) and then the endothelium-dependent release is assessed as a response to different concentrations of acetylcholine (0.1 μM; 1.0 μM; 10.0 μM)

Results

A) Contraction (g) from Norepinephrine (Range 100÷10,000 nM)

|  | Norepinephrine 100 nM | Norepinephrine 1,000 nM | Norepinephrine 10,000 nM |
| --- | --- | --- | --- |
| Group 1 | 0.40 | 0.78 | 1.35 |
| Group 2 | 0.20 | 0.40 | 0.70 |
| Group 3 | 0.20 | 0.40 | 0.70 |
| Group 4 | 0.21 | 0.39 | 0.72 |
| Group 5 | 0.22 | 0.41 | 0.69 |
| Group 6 | 0.45 | 0.80 | 1.45 |

B) Vascular Tone-% of Pre-Contraction from Acetylcholine (Range 0.1÷10 μM)

|  | Acetylcholine 0.1 μM | Acetylcholine 1.0 μM | Acetylcholine 10.0 μM |
| --- | --- | --- | --- |
| Group 1 | 85% | 75% | 65% |
| Group 2 | 99% | 94% | 85% |
| Group 3 | 100% | 96% | 81% |
| Group 4 | 98% | 95% | 80% |
| Group 5 | 100% | 95% | 80% |
| Group 6 | 82% | 72% | 53% |

The data reported in the tables clearly show a synergistic effect found only with the administration of the PEA-Rutin micro-compound (Groups 1 and 6), especially when compared with the separate administration of PEA and Rutin, both separately micronized (Group 4).

The composition additionally containing an antioxidant (hydroxytyrosol, Group 6) shows greater than the PEA-Rutin micro-compound only (Group 1).

The invention will now be further described by means of the following example formulations.

FORMULATION EXAMPLES

Example 1

One tablet contains:

| PEA-Rutin micro-compound (5:1 ratio) | mg | 360.0 |
| --- | --- | --- |
| Pure hydroxytyrosol | mg | 15.0 |
| Maltodextrin | mg | 60.0 |
| Microcrystalline cellulose | mg | 80.0 |
| Croscarmellose sodium | mg | 24.0 |
| Polyvinylpyrrolidone | mg | 10.0 |
| Magnesium stearate | mg | 5.0 |
| Colloidal anhydrous silica | mg | 4.0 |
| Coating & dye | mg | 34.0 |

Example 2

One oily soft gelatin capsule contains:

| PEA-Rutin micro-compound (ratio 1:1) | mg | 300.0 |
| --- | --- | --- |
| Pure hydroxytyrosol | mg | 30.0 |
| Soy lecithin | mg | 50.0 |
| α-Tocopherol (%) | mg | 30.0 |
| Vegetable oil | mg | 200.0 |

Example 3

One hard gelatin capsule contains:

| PEA-Rutin micro-compound (ratio 5:2) | mg | 520.0 |
| --- | --- | --- |
| Pure glycyrrhetinic acid | mg | 25.0 |
| Lactose | mg | 200.0 |

Example 4

One tablet contains:

| PEA-Rutin micro-compound (ratio 5:1) | mg | 450.0 |
| --- | --- | --- |
| Pure maslinic acid | mg | 35.0 |
| Vegetable polysorbate | mg | 4.0 |
| Microcrystalline cellulose | mg | 140.0 |
| Croscarmellose sodium | mg | 80.0 |
| Polyvinylpyrrolidone | mg | 40.0 |
| Magnesium stearate | mg | 8.0 |
| Colloidal anhydrous silica | mg | 4.0 |
| Coating & dye | mg | 30.0 |

Example 5

One sachet of micro-granules for sublingual use contains:

| PEA-Rutin micro-compound (ratio 1:1) | mg | 600.0 |
| --- | --- | --- |
| Pure hydroxytyrosol | mg | 45.0 |
| Sorbitol | mg | 350.0 |
| Polysorbate 80 | mg | 3.0 |
| Palmitic esters of sucrose P-1570 | mg | 12.5 |

Example 6

10 ml of oral suspension contain:

| | | |
|---|---|---|
| PEA-Rutin micro-compound (ratio 5:1) | mg | 500.0 |
| Oleoeuropein | mg | 20.0 |
| Soy lecithin | mg | 20.0 |
| Carboxymethylcellulose | mg | 200.0 |
| Preservative and flavoring | as needed to | 10.0 ml. |

Example 7

One tablet contains:

| | | |
|---|---|---|
| PEA-Rutin micro composite (ratio 5:1) | mg | 360.0 |
| Ursolic acid | mg | 30.0 |
| Corn dextrins | mg | 60.0 |
| Microcrystalline cellulose | mg | 80.0 |
| Croscarmellose sodium | mg | 24.0 |
| Polyvinylpyrrolidone | mg | 10.0 |
| Magnesium stearate | mg | 5.0 |
| Colloidal anhydrous silica | mg | 4.0 |

What we claim is:

1. A method of treatment, in humans and animals, of diseases of arteries and arterioles associated with aging and primary dysmetabolic diseases, comprising administering an effective amount of a composition consisting of a mixture of palmitoyl-ethanolamide (PEA) and Rutin in the co-micronized form and optionally an antioxidant molecule with a triterpene structure and optionally phytochemical compounds characterized by an ORAC (Oxygen Radical Absorption Capacity) index higher than 35,000-40,000 µmolTE/g, wherein the mixture of PEA and Rutin in the co-micronized form have a PEA/Rutin weight ratio between 10:1 and 1:1.

2. The method according to claim 1, wherein the mixture of palmitoyl-ethanolamide (PEA) and Rutin in the co-micronized form has a particle size distribution, measured by a Malvern Mastersizer 3000 instrument with Fraunhofer calculation algorithm, wherein at least 90% by volume of particles has a particle size of less than 10 microns.

3. The method according to claim 1, wherein the mixture of palmitoyl-ethanolamide (PEA) and Rutin in the co-micronized form has a particle size distribution, measured by a Malvern Mastersizer 3000 instrument with Fraunhofer calculation algorithm, having a mode between 2 and 4 microns and having at least 94% by volume of particles smaller than 10 microns or at least 50% by volume of particles smaller than 4 microns.

4. The method according to claim 1, wherein the antioxidant molecule is selected from the group consisting of glycyrrhetinic acid, maslinic acid, and ursolic acid.

5. The method according to claim 1, wherein the phytochemical compounds are selected from the group consisting of hydroxytyrosol or natural conjugates thereof.

6. The method according to claim 1, wherein the weight percentage of antioxidant molecules and/or phytochemical compounds in the composition is between 1% and 10%.

7. The method according to claim 1, wherein said diseases are selected from the group consisting of:
Atherosclerosis/Arteriosclerosis;
Aortic aneurysms of different localization;
Neointimal hyperplasia of different etiology;
Vascular complications associated with the hypokinetic syndrome of the elderly; and
Vascular complications associated with the diabetic metabolic syndrome.

8. The method according to claim 1, wherein the composition is a human or veterinary pharmaceutical formulation, or a dietary composition, a food supplement or feed or nutritional supplement for animals.

9. The method according to claim 1, wherein the composition is formulated in dosage forms for oral, buccal, parenteral, rectal, or transdermal administration.

10. The method according to claim 1, wherein the mixture of PEA and Rutin in the co-micronized form is administered in amounts between 10 mg and 1000 mg per dose unit.

11. A dietary composition, food supplement, or food for special medical purposes (FSMP), or feed, or nutritional supplements for animals, comprising the composition according to claim 1.

* * * * *